US010130327B2

(12) United States Patent
Carlsson

(10) Patent No.: US 10,130,327 B2
(45) Date of Patent: Nov. 20, 2018

(54) RADIOTHERAPY APPARATUS

(71) Applicant: Elekta AB (publ), Stockholm (SE)

(72) Inventor: Per Carlsson, Stockholm (SE)

(73) Assignee: Elekta AB (publ), Stockholm (SE)

( * ) Notice: Subject to any disclaimer, the term of this patent is extended or adjusted under 35 U.S.C. 154(b) by 191 days.

(21) Appl. No.: 13/743,610

(22) Filed: Jan. 17, 2013

(65) Prior Publication Data

US 2013/0188767 A1   Jul. 25, 2013

Related U.S. Application Data

(60) Provisional application No. 61/588,376, filed on Jan. 19, 2012.

(51) Int. Cl.
*A61N 5/00* (2006.01)
*A61B 6/00* (2006.01)
*A61B 6/03* (2006.01)
*A61N 5/10* (2006.01)

(52) U.S. Cl.
CPC .............. *A61B 6/542* (2013.01); *A61B 6/032* (2013.01); *A61B 6/035* (2013.01); *A61N 5/1037* (2013.01)

(58) Field of Classification Search
CPC . A61N 5/00; A61N 5/10; A61N 5/103; A61N 5/1071; A61N 5/1037; A61N 5/1048; A61N 5/1049; A61N 5/1064; A61B 6/032; A61B 6/542
USPC ..................................... 378/65, 147, 207, 62
See application file for complete search history.

(56) References Cited

U.S. PATENT DOCUMENTS

| | | | |
|---|---|---|---|
| 7,596,207 B2* | 9/2009 | Kaus ..................... | A61N 5/103 378/62 |
| 2005/0251029 A1* | 11/2005 | Khamene ............. | A61B 8/4245 600/427 |
| 2009/0110145 A1* | 4/2009 | Lu .......................... | A61N 5/103 378/65 |
| 2009/0114846 A1* | 5/2009 | Blankenbecler ........... | 250/492.1 |
| 2009/0213991 A1* | 8/2009 | Brown et al. .................. | 378/65 |
| 2010/0088339 A1* | 4/2010 | Rietzel .................. | A61N 5/103 707/780 |
| 2010/0127184 A1* | 5/2010 | Balakin ................ | A61N 5/1049 250/396 R |
| 2010/0228116 A1* | 9/2010 | Lu .......................... | A61N 5/103 600/411 |
| 2011/0112351 A1* | 5/2011 | Fordyce, II ............ | A61N 5/103 600/1 |

(Continued)

FOREIGN PATENT DOCUMENTS

WO    WO 2009/055775 A2    4/2009    ............. A61B 19/00

OTHER PUBLICATIONS

European Patent Office, European Search Report, 12000283.7-2305, dated Apr. 19, 2012, 5 pages.

*Primary Examiner* — Wyatt Stoffa
(74) *Attorney, Agent, or Firm* — Sunstein Kann Murphy & Timbers LLP

(57) ABSTRACT

Intra-fraction movement of the patient puts at risk sensitive regions that are near to a radiation dose. In a radiotherapy system that delivers a dose as a series of discrete sub-doses, an initial CT scan is performed to determine the patient's position, after which the sub-doses that are directed to regions within a preset distance of a sensitive structure are performed first, while the sub-doses directed to regions that are more remote from a sensitive structure are performed later.

9 Claims, 3 Drawing Sheets

(56) References Cited

U.S. PATENT DOCUMENTS

| | | | |
|---|---|---|---|
| 2011/0150173 A1* | 6/2011 | Shinno | A61B 6/032 378/5 |
| 2011/0180731 A1* | 7/2011 | Welsh | A61N 5/103 250/492.3 |
| 2013/0018232 A1* | 1/2013 | D'Souza | A61B 6/12 600/300 |

* cited by examiner

RADIOTHERAPY APPARATUS

This application claims priority from U.S. Provisional Patent Application 61/588,376, filed Jan. 19, 2012, which is incorporated herein by reference.

TECHNICAL FIELD

The present invention relates to radiotherapy.

BACKGROUND ART

Radiotherapy consists of directing beams of ionizing radiation toward a tumor. The radiation (usually high-energy x-rays) is absorbed by the tumor cells causing cell damage. Obviously, the radiation is also capable of damaging the healthy tissue around the tumor, so various techniques are used in order to limit this. The dose is usually delivered in time-separated fractions (i.e. individual treatment sessions), allowing the healthy tissue to recover between fractions, and the doses are carefully collimated so that the amount of healthy tissue that is irradiated is minimized.

Within a single fraction, the dose may be delivered from a number of different directions so that the dose to each region of healthy tissue is reduced. This can be delivered in discrete stages, with the radiation source being repositioned after each stage, or the source can be moved continuously around the patient during delivery of the dose.

Where a beam of radiation is being collimated to a specific area, that area will of course be one that is defined relative to the anatomy of the patient. Therefore, the location of the patient needs to be established in advance of treatment so that the beam can be appropriately directed. Usually, a CT scan of the patient (by which we mean to include both a fan- or pencil-beam slice-by-slice CT scan or a CBCT scan, or "cone-beam CT" scan) will be taken immediately prior to each fraction of a fractionated treatment, while the patient is on the couch ready for treatment. This will identify the patient's exact location with accuracy. Modern radiotherapy machines include cone-beam CT scanning capability to permit this.

SUMMARY

A cone-beam CT scan at the start of a fraction deals with inter-fraction movement of a patient (i.e. movement that takes place between the end of one fraction, or treatment session, and the start of the next fraction). However, it does not prevent or reveal intra-fraction movement (i.e. movement that takes place during the delivery of a single treatment fraction). Patients can be asked to lie still, but are generally only able to do so with the accuracy required for a limited period of time. The patient can be restrained, but this is uncomfortable and only particularly effective for regions such as the head and upper neck where there is a hard structure (the skull) whose immobilization will fix the local anatomical structures.

Away from such areas, there are still a number of sensitive regions whose irradiation should be avoided. These are (generally) regions that are especially prone to radiation damage, and/or linear organs where damage anywhere along the organ prevents the functioning of a large part of the organ. Examples include the spinal cord, the optic nerve, the intestines, and the like. Many of these are in anatomical regions that are easily moved by the patient, which would mean that a sensitive region could be placed into the beam.

One option would be to perform continuous or frequent CT scans, but each scan involves delivering a radiation dose to the whole region. In general, it is desirable to limit this exposure for each patient, so if (or to the extent that) this can be avoided, it would be advantageous to do so.

The present invention seeks to combine confidence as to the correct positioning of the patient with the limitation of the number of CT scans that need to be delivered. The position of the patient's treatment volume is certain at the CBCT scan or directly thereafter, whereas it becomes more and more uncertain as time passes, i.e. the probability of movement of treatment volume increases with time. In essence, the invention is applicable to radiotherapy systems that deliver that fraction's dose in a series of individual doses, and provides that an initial CT scan is performed to determine the patient's position, after which the individual doses that are directed to regions within a preset distance of a sensitive structure are then performed first, while individual doses directed to regions that are more remote from a sensitive structure are performed later. In this way, the doses for which the patient position is most critical are performed while the level of confidence in the patient position is at its highest, whereas later in the fraction when the patient position is less certain, the sub-doses whose exact positioning is less critical are delivered.

In a particular treatment, it may be that there are too many "near-sensitive" doses to deliver these within a reasonable time after the initial CT scan. Thus, in a preferred form of the invention, there is a post-CT time limit after which a "near-sensitive" dose may not be delivered, and if all the "near-sensitive" doses cannot be delivered within this time then a further CT scan or scans are scheduled for later in the fraction, with the remaining "near-sensitive" doses being delivered within the time limit after that CT scan. A suitable time limit could be 15 minutes, such as between 8 and 20 minutes, but will depend on the localization of the target and on the patient and will thus need to be assessed by a clinician.

The radiotherapy apparatus can be arranged to allow a user (such as a clinician) to highlight the critical individual doses, i.e. those directed to a region within a preset distance of a sensitive structure or could calculate as a sensitivity analysis those doses that will contribute most to the sensitive region dose if they are moved. Alternatively, the user could highlight the sensitive structures and the apparatus could classify those individual doses that are within a certain distance. Many radiotherapy treatment planning systems include the facility to classify regions as being sensitive in order to take this into account in planning the shapes and direction of delivery of the sub-doses, so this information may already be available to the system. As a further alternative, the system could allow a user to rank the individual doses in order of sensitivity.

Typically, a radiotherapy delivery system has an associated treatment planning system that accepts the physical and mechanical (etc.) constraints of the delivery system, the intended dose distribution, the details of the patient's anatomy, a definition of the target region and any sensitive regions that need to be avoided, and produces a treatment plan comprising a set of instructions for the delivery system as to the nature, shape and direction of the radiation beams to emit. The above can be an additional constraint for the treatment planning system to take into account; once the treatment plan is finalized, an additional step can be carried out in either ranking the individual doses or allowing them to be ranked and checking for compliance with the time limit.

DETAILED DESCRIPTION

Figure 1:
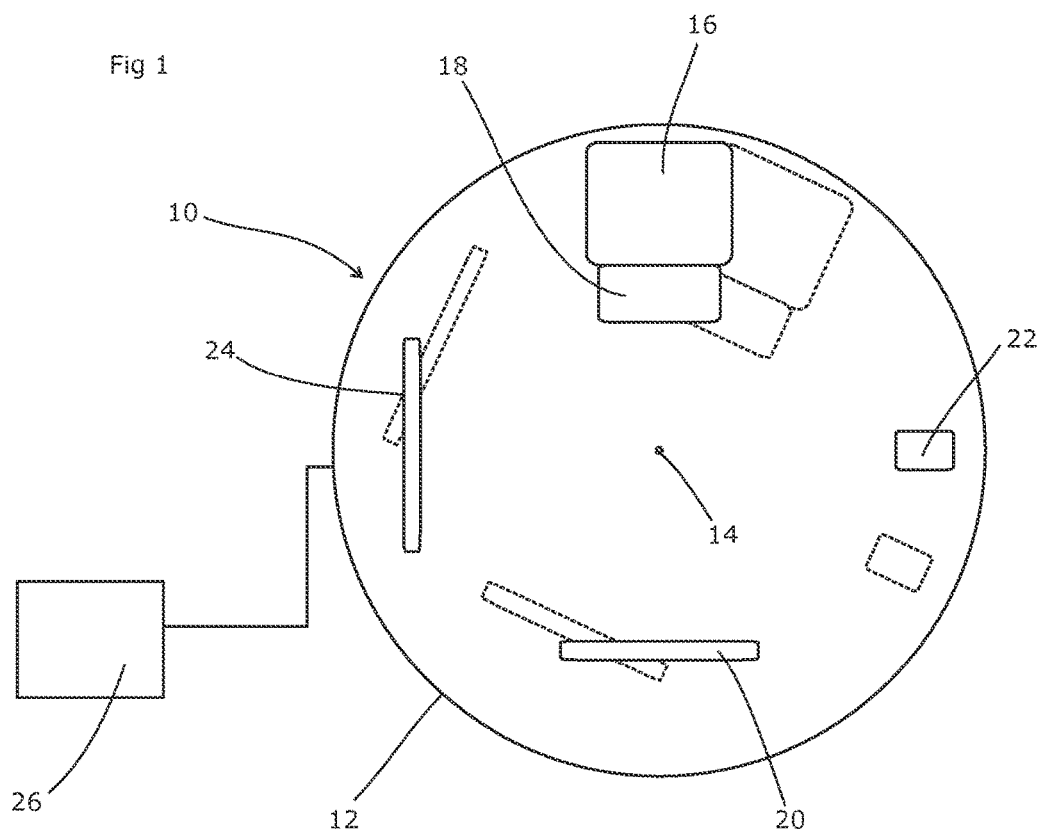
FIGS. 1 and 2 show (respectively) a front and side view of a first example of a radiotherapy apparatus suitable for use in the present invention.
Figure 2:
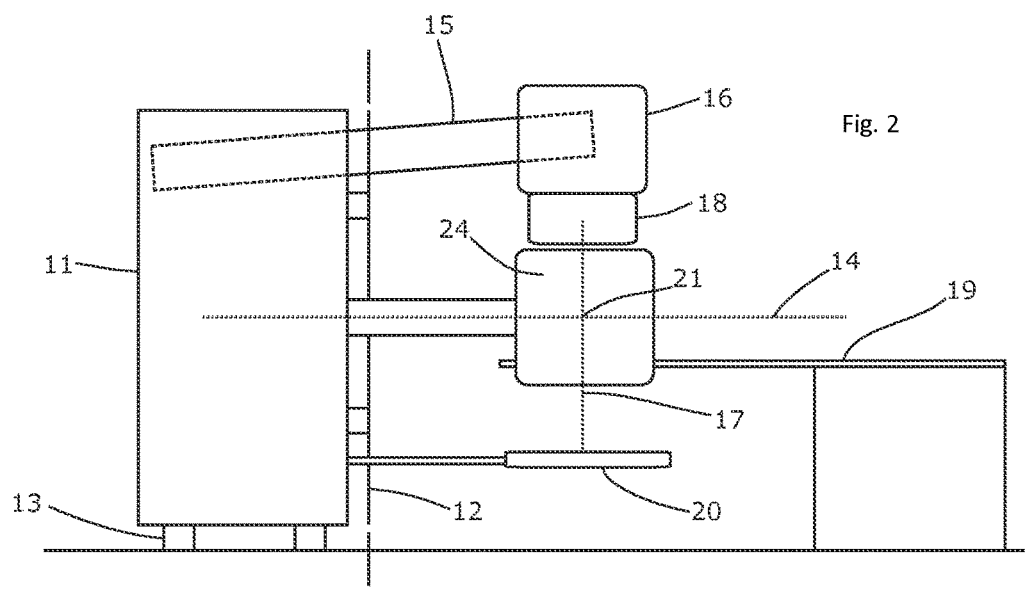

Referring to FIGS. 1 & 2, a radiotherapy apparatus 10 comprises a rotatable faceplate 12 which is generally circular and mounted on a suitably substantial rotatable base 11. An arrangement of bearings and drives 13 allow the base 11 to rotate around a central horizontal axis 14 in a generally known manner.

A linear accelerator 15 is built into the base 11 and extends forward from the support at an off-centre position, ending in a source of megavoltage (MV) therapeutic X-radiation 16 directed radially inwardly towards the rotation axis 14. Collimation apparatus 18 is provided on the source 16, in a generally known manner so as to shape the beam as required. A patient can be supported on an adjustable table 19, positioned so that a target region is located approximately at the point of intersection of the rotational axis 14 and the centreline 17 of the beam emitted by the source 16 (a point known as the "isocenter" 21). The base 11 can then be rotated around the patient, allowing the source 16 to irradiate the patient from a variety of directions. In this way, the dose to the target region can be maximised whilst minimising the dose to the surrounding healthy tissue.

A megavoltage imaging panel 20 is provided, supported from the base 11 diametrically opposite the MV source 16. This captures an image from the radiation emitted by the source 16 as attenuated by the patient and can provide useful information as to the internal structure of the patient.

Many radiotherapy apparatus also include a diagnostic kV source 22. This is also mounted on the base 11, typically located 90 degrees away from the MV source 16. Collimation can be provided for this source, usually static in nature, in order to limit the beam to the desired aperture size. A corresponding flat panel two-dimensional kV imaging panel 24 is also provided, diametrically opposite the kV source 22. These can be used to capture radiographs of the relevant region of the patient; a number of such images can be captured and combined to produce a computed-tomography (CT) scan using known techniques.

A control unit 26 serves to control the radiation sources 16, 22, the collimator 18, the flat panel imagers 20, 24, the support 12, and other equipment that may be provided as required. This control is exercised in line with a "treatment plan" developed in advance based on knowledge of the patient anatomy, the tumor location, the properties of the beam produced by that source 16, the constraints of the collimator 18 and the other items of equipment (such as the range of movement of the table 19) etc. Typically, the treatment plan is created overnight prior to the treatment by dedicated treatment planning computers which accept these constraints and use known software and algorithms to generate a treatment plan.

Figure 3:
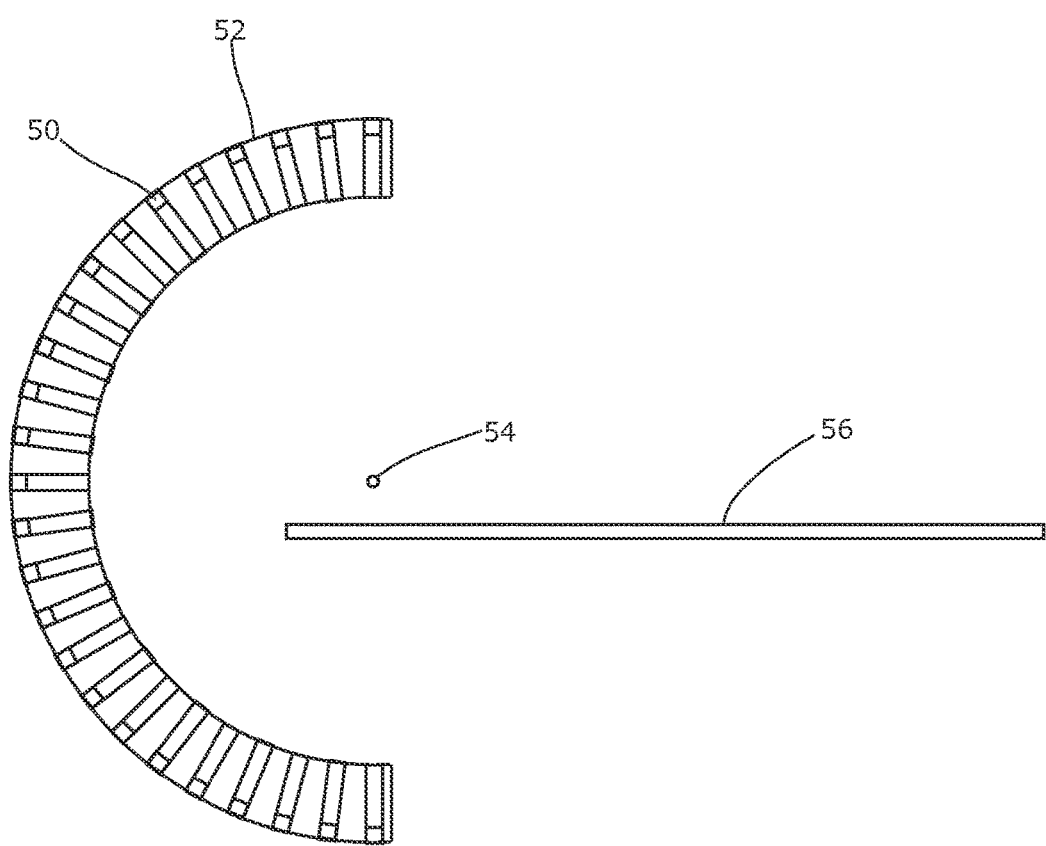
FIG. 3 shows a side view of a second example of a radiotherapy apparatus suitable for use in the present invention.

An alternative delivery system is illustrated in FIG. 3, showing a multiple-source radiotherapy apparatus in the form of a Leksell Gamma Knife™. This typically contains 192 Cobalt-60 sources 50, each of approximately 30 curies (1.1 TBq), each placed on a sector arrangement of eight sectors in a semi spherical configuration in a heavily shielded assembly 52. Each source is collimated by the assembly 52 and aims gamma radiation at a target point 54. Collimators (not shown) allow the sources to be exposed during treatment or concealed while the patient is being positioned by moving the sectors to an off position. All collimators aim at the same position in space, the target.

A patient can be supported on a table 56 so as to locate the tumor at the target point 54. Each individual beam is of relatively low intensity, so the radiation has little effect on intervening brain tissue and is concentrated only at the tumor itself Once the patient is positioned, the collimators are opened for the required period of time in order to deliver an individual dose. The sources are then put to an off position while moving the patient to the next position where dose is to be delivered. Normally all sources are delivering dose simultaneously, though some can be blocked allowing only a subset of the sources to deliver a dose for one or more patient positions.

Historically, the Gamma Knife has been used for cranial tumors, which have a stable location relative to hard structures around them such as the skull. Accordingly, it is common to fixate the patient's skull using known frames that can be securely attached to the patient support. Movement of the tumor during a fraction can therefore be discounted. However, it is being proposed that Gamma Knife systems be used for treating tumors in the neck and upper shoulders, where there is no suitable fixed structure that has a rigid relationship with the tumor. Also, these areas include the spinal cord, which must not be accidentally irradiated.

Whatever form of delivery method is used, it is necessary to develop a treatment plan setting out the doses of radiation that are to be delivered, which achieves the prescribed dose while remaining within the various constraints. The patient-imposed constraints on the treatment plan are generally derived from classifying (or "segmenting") the volume of the patient into one of three categories:

a) tumor tissue, into which the prescribed dose is to be delivered. This dose may be uniform, or may consist of different doses in different areas. Generally, a margin of healthy tissue around the actual tumor volume is also included within this category, to allow for minor movement of the tumor and/or patient during treatment and for scanning tolerances, b) Ordinary tissue such as muscle, skin, bone and resilient organs such as the liver, into which the delivered dose is to be limited so far as possible, and c) Sensitive volumes such as eyes, the optic nerve, the spinal cord etc., into which the delivered therapeutic dose is to be substantially zero.

Other constraints arise from the nature of the delivery method and (obviously) the dose distribution to be achieved. These constraints are then provided to the treatment planning computer, which produces a treatment plan consisting of instructions for the radiotherapy apparatus.

The treatment plans for some systems consist of a series of individual doses that are to be delivered to the patient. The main alternative is, for example, a single dose that is delivered from a source that moves and/or adjusts its collimation during the fraction (such as VMAT-based techniques). In either case, the treatment will take a period of time to deliver, and is created on the assumption that the patient remains stationary throughout. This assumption may not be valid, depending on the time required and the particular patient. Generally, up-to-date radiotherapy apparatus comprises a CBCT functionality together with the irradiation equipment. This allows a CBCT scan to be taken at the start of the fraction in order to locate the patient (by corresponding compensatory adjustment of the patient support), and either the CBCT scan will be repeated after intervals in order to update the position of the patient (and, if necessary, correct it) or some form of fixation device will be used to immobilise the patient. The latter can be uncomfortable, and the former is in principle undesirable unless absolutely necessary, as a CBCT scan involves delivering a non-trivial dose of radiation to the entire volume. Some systems provide a conventional CT scanner which is incorporated within the radiotherapy apparatus; the following discussion is also valid for a such an arrangement, using a CBCT scan instead.

In treatment plans of the former type, i.e. those consist of a series of individual doses, the present invention allows fewer CBCT scans to be used whilst still having the necessary degree of confidence. This is based on the realisation that the likelihood of a certain amount of movement by the patient increases with time, therefore those individual doses for which the patient positioning is most critical should be scheduled earliest after a CBCT scan, and those for which the patient position is not so critical can be scheduled later. Thus, by classifying an individual dose according to its proximity to a sensitive structure, a decision can be made as to where in the sequence of that fraction the individual dose should be scheduled.

That classification can be a binary decision, i.e. that the individual dose is within a certain distance of a critical structure or that it is not. Alternatively, the classification can be a system describing which range of distances the individual dose falls into, such as "very close", "proximate" or "distant", which may be coded as "1", "2" or "3". In a further alternative, the closest approach distance of the dose to a sensitive structure could be employed to provide an analogue scale.

Another way of classifying individual doses could be to let the treatment planning system perform a sensitivity analysis for each of the doses to be delivered ("shots"), whereby the effect of varying a shot position is determined automatically and the increase of dose to the sensitive tissue is calculated. This allows the relative importance of positional accuracy to be determined for each of the shots, in terms of the potential sensitivity of a positional error in a specific shot. The shot at the position with the largest contribution to dose in sensitive tissue when that shot is moved is thereafter selected to be delivered first, as it presents the highest risk if there should be a movement or positioning error. More generally, the shots can be ranked into an order for delivery by a suitable algorithm. For example, if there are six shots ranked in decreasing order of sensitivity as shots 1-6, these could be delivered in the order [CBCT scan], 1, 2, 3, 4, 5, 6, so that the most positionally sensitive are placed first. If there is insufficient time after the scan to deliver these, then al alternative order such as [CBCT scan], 1, 3, 5, [CBCT scan], 2, 4, 6 can be adopted (etc.).

The classification could be done automatically by the treatment planning computer, based on its knowledge of the individual dose locations and the locations of the sensitive structures. Alternatively, a suitably skilled user could classify the individual doses. Some classification systems will of course be better suited to automation, and some to user selection.

Figure 4:
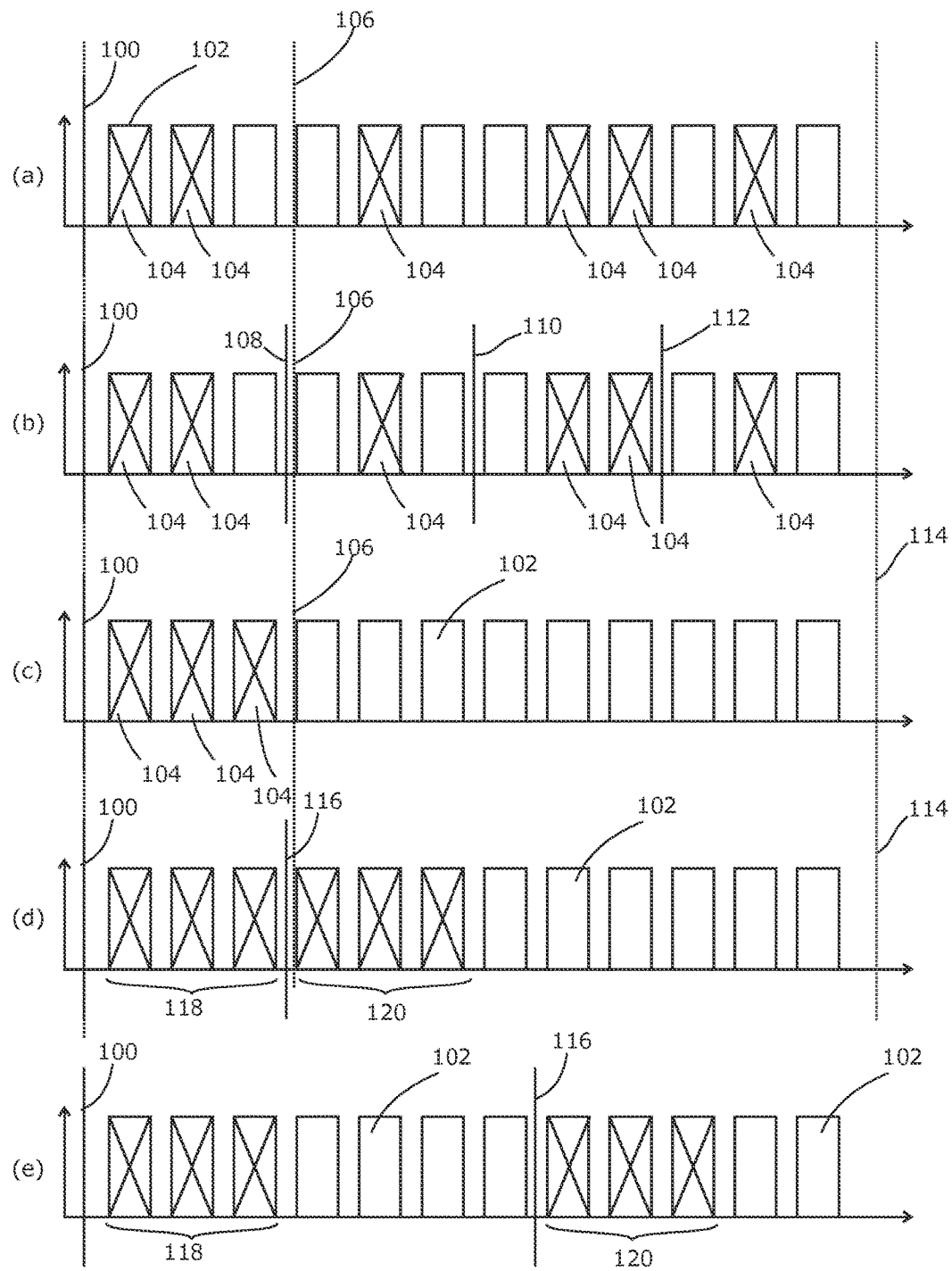
FIGS. 4(a) to 4(e) show in schematic form alternative treatment plans, illustrating the nature and benefits of the present invention.

FIG. 4 shows the effect of implementing a binary classification system on a simple treatment plan consisting of 12 individual doses, of which 6 are near to a sensitive structure. FIG. 4(a) shows a known arrangement. An initial cone-beam CT scan 100 is performed, followed by a series of individual doses 102. Highlighted doses 104 are proximate a sensitive structure, and are distributed throughout the treatment fraction. If we assume (for the sake of illustration) that after a period of time equivalent to three individual doses, there is a significant risk that the patient has moved an amount that is enough to place a sensitive structure at risk, then this means that many of the highlighted doses are outside this safe region 106. On this basis, the plan shown in FIG. 4(a) exhibits an unacceptable risk in that the later doses will be delivered without adequate confidence in the location of the patient. Therefore, to assure safety, three additional CBCT scans 108, 110 and 112 must be performed as shown in FIG. 4(b) so that all the highlighted doses are within this safe period of time.

Of course, the particular period of time chosen may be different, and individual doses may be of different exposure times, meaning that the chosen period may not correspond to an exact number of individual doses. However, the principle can be illustrated in this way.

FIG. 4(c) shows a first embodiment of the invention. The highlighted doses 104 are all grouped together at the start of the treatment, and are followed by the remaining doses 102. Thus, those doses 104 that are proximate to sensitive areas of the patient are delivered within the safe region 106 after the initial CT scan 100. The other doses are delivered within a longer period 114 during which it is safe to assume that the patient has not moved so far as to render those doses unsafe, although the patient may have moved too far for a near-sensitive dose to be considered unsafe.

In FIG. 4(c), there are of course fewer near-sensitive doses 104 than in the preceding examples of FIGS. 4(a) and 4(b), reflecting the fact that the safe period after the initial CT scan 100 is (in this case) only sufficient to allow three individual doses to be delivered. To deliver more, an additional CT scan 116 needs to be performed into order to "re-set" the patient position, establishing this with confidence and allowing further near-sensitive doses to be delivered. This can be done as in FIG. 4(d) or 4(e).

FIG. 4(d) shows the additional CT scan 116 being performed immediately after the expiry of the safe period 106. This means that a first group 118 of near-sensitive doses can be delivered immediately after the initial CT scan 100, followed by the additional CT scan 116, followed by a second group 120 of near-sensitive doses, followed by the remaining individual doses 102.

FIG. 4(e) shows an alternative implementation of the invention, in which the first group 118 of near-sensitive doses is again delivered immediately after the initial CT scan 100, but is followed by some of the "ordinary" doses 102. These are followed by the additional CT scan 116, which is then followed by a second group 120 of near-sensitive doses, followed by the remaining individual doses 102. This allows the additional CT scan (or scans) 116 to be distributed more evenly through the fraction, meaning that all doses are delivered more promptly after a CT scan. Note that in FIG. 4(e), the longest period between a CT scan and an individual dose is 7 doses, as opposed to 9 doses in FIG. 4(d). Both FIGS. 4(d) and 4(e) require only two CT scans, however, compared to four scans in FIG. 4(b).

Table 1 shows another example. In this example, individual doses or "shots" are ranked according to their level of criticality by a clinician on a scale of 1 to 3. These are then scheduled for delivery in order, with the highest ranked (level 1) first. This reveals that there is insufficient time to deliver all the ranked shots within a safe period after the initial cone-beam CT scan, so they are divided into two groups with an additional CT scan prior to the second group. To further optimise the delivery, the category "1" shots are divided into two sub-groups and each sub-group is placed at the start of its respective group, thereby ensuring that the shots with the highest level of criticality are delivered soonest after a CT scan, and so one for the level "2" shots. The level "3" shots are then distributed among the groups so as to remain within the safe periods after a CT scan and minimise the times spent on each group. The result of this optimisation is set out in table 1.

TABLE 1

|  | Criticality | Time (minutes) CBCT |
|---|---|---|
| Critical shots | 1 | 1.8 |
|  | 1 | 1.3 |
|  | 2 | 1.4 |
|  | 3 | 1.8 |
|  | 3 | 1.2 |
|  | 1 | 2 |
|  | 2 | 2.5 |
|  | 2 | 1.4 |
| Normal Shots | — | 3 |
|  | — | 5 |
|  | — | 8 |

Thus, the present invention allows individual doses within a treatment fraction to be delivered with greater confidence as to the patient position, without having to incur unnecessary CBCT-related doses. This is able to improve the accuracy to target to probably sub-millimeter in respect of the critical shots, thereby making a single session possible when using the Elekta LGK PERFEXION system, without requiring an IFMM (intra-fraction motion management) solution.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of developing and implementing a radiotherapy treatment plan for a patient via a radiotherapy delivery system that delivers a fraction dose in a series of individual doses, each individual dose directed to a location within the patient, the method comprising:
    providing an initial CT scan to determine the patient's position,
    developing the radiotherapy treatment plan setting out the series of individual doses to be delivered to the patient, and a classification of relative importance of positional accuracy for each of the individual doses and their associated location in terms of potential sensitivity of a positional error to irradiation, the classifications based on constraints including:
        at least one sensitive region within the patient including sensitive tissue especially prone to radiation damage and irradiation of which is to be avoided,
        at least one ordinary tissue region within the patient including ordinary tissue in which irradiation is allowed to be limited, and
        at least one target irradiation region within the patient that is to be irradiated;
    wherein setting out the series of individual doses to be delivered includes:
        scheduling individual doses, directed to locations within a target irradiation region with closest proximity to the at least one sensitive area and thus having greatest relative importance of positional accuracy, to be delivered first, and
        scheduling subsequent individual doses directed to locations within the target irradiation region in decreasing order of relative importance; and
    delivering the series of individual doses based, at least in part, on the radiotherapy treatment plan and the initial CT scan.

2. A method according to claim 1, wherein a location has greatest relative importance of positional accuracy when it is within a preset distance of the at least one sensitive region.

3. A method according to claim 1, wherein a location has greatest relative importance of positional accuracy when it is marked by a user as being proximate to the at least one sensitive region.

4. A method according to claim 1 wherein the treatment plan includes further CT scans to be performed within the fraction, and wherein delivering the series of individual doses is based on the radiotherapy treatment plan, the initial CT scan, and the further CT scans.

5. A method according to claim 4, wherein the treatment plan includes a defined time limit subsequent to a CT scan, after which an individual dose that is directed to a location with greatest relative importance of positional accuracy may not be delivered.

6. A method according to claim 5, including:
    calculating a delivery time required for the doses directed to locations with greatest relative importance of positional accuracy;
    comparing the delivery time to a pre-defined time limit,
    if the delivery time is greater than the pre-defined time limit, inserting a further CT scan into the treatment plan; and
    scheduling at least some of the remaining individual doses directed to a location with greatest relative importance of positional accuracy after the further CT scan.

7. A method according to claim 5 in which the time limit is between 8 and 20 minutes.

8. A method according to claim 5 in which the time limit is approximately 10 minutes.

9. A method of developing and implementing a radiotherapy treatment plan for a patient via a radiotherapy delivery system that delivers a fraction dose in a series of individual doses, each individual dose directed to a location within the patient, the method comprising:
    developing the radiotherapy treatment plan, the treatment plan including details of a plurality of CT scans to be performed within the fraction, the treatment plan setting out the series of individual doses to be delivered to the patient and a classification of relative importance of positional accuracy for each of the individual doses and their associated location in terms of potential sensitivity of a positional error to irradiation, the classifications based on constraints including:
        at least one sensitive region within the patient including sensitive tissue especially prone to radiation damage and irradiation of which is to be avoided,
        at least one ordinary tissue region within the patient including ordinary tissue in which irradiation is allowed to be limited,
        at least one target irradiation region within the patient that is to be irradiated;
    wherein the radiotherapy treatment plan includes:
        a first CT scan that determines the patient's position, subsequently, thereto, scheduling a plurality of individual doses that first are directed to locations within a target irradiation region with greatest relative importance of positional accuracy, subsequently thereto, a second CT scan that determines the patient's position, and subsequently thereto, scheduling at least one individual dose that is directed to other locations in decreasing order of relative importance of positional accuracy; and delivering the series of individual doses based on the radiotherapy treatment plan and the first and second CT scans.

\* \* \* \* \*